United States Patent [19]

Cava et al.

[11] Patent Number: 4,489,206

[45] Date of Patent: Dec. 18, 1984

[54] SYNTHESIS OF (+)-4-DEMETHOXYDAUNOMYCINONE

[75] Inventors: Michael P. Cava, Wynnewood, Pa.; Domingo Dominguez, Santiago de Compostela, Spain

[73] Assignee: Adria Laboratories, Inc., Columbus, Ohio

[21] Appl. No.: 494,247

[22] Filed: May 13, 1983

[51] Int. Cl.³ .................... C07C 50/36; C07D 303/37
[52] U.S. Cl. ................ 549/543; 260/351.1; 260/351.5; 260/365; 260/376
[58] Field of Search ................. 260/351.1, 351.5, 325, 260/376; 549/543

[56] References Cited

U.S. PATENT DOCUMENTS 4,229,355 10/1980 Penco et al. .................... 549/543
4,298,535 11/1981 Vogel et al. .................... 260/365

FOREIGN PATENT DOCUMENTS 2601785 7/1976 Fed. Rep. of Germany ...... 260/365

OTHER PUBLICATIONS

*Tetrahedron Letters,* No. 27, pp. 2303–2306, "Synthesis of Anthracyclinones via Base-Catalyzed Cyclizations of Dihydroanthraquinone Dev.", Suzuki et al., 1977.
*Tetrahedron Letters,* vol. 21, pp. 2753–2756, "Asymmetric Synthesis of Optically Pure (R)(−)-2-acetyl-5,-8-Dimethoxy-1,2,3,4-tetrahydro-2-napthol", Terashima, 1980.
*Canadian Journal of Chemistry,* vol. 49, pp. 2712–2718, "Synthetic Studies of Hydronapthaceric Antibiotics", Wong et al., 1971.
*JACS,* vol. 100, No. 11, pp. 3635–3636, "A Novel Synthesis of (±)-4-Demethoxydaunomycinone" Kerdesky et al., 1978.
*Canadian Journal of Chemistry,* vol. 51, pp. 466–467, "The Total Synthesis of Daunomycinone" Wong et al., 1972.
*J. Chem. Soc. Chem. Commun.,* 1982, pp. 158–160, Broadharet et al.
*J. C. S. Chem. Commun.,* 1981, pp. 1100–1101, "Preparation of (−)-(7R) Acetyl-7-Hydroxy-4,4-dimethoxy-5,6,7,8-tetrahydronaphthalen-1 (4H)-one", Warrener, 1981.

*Primary Examiner*—Glennon H. Hollrah
*Assistant Examiner*—Raymond Covington
*Attorney, Agent, or Firm*—Marion C. Staves

[57] ABSTRACT

It has been found that stereospecific R(−)-4-demethoxy-7-deoxydaunomycinone can be synthesized from the known compound 4-demethoxy-7,9-dideoxydaunomycinone. R(−)-4-Demethoxy-7-deoxydaunomycinone is an intermediate in the synthesis of (+)-4-demethoxydaunomycinone, the aglycone of the nonnaturally occurring and antitumor active (−)7(S)9(S)-4-demethoxydaunorubicin.

5 Claims, No Drawings

SYNTHESIS OF (+)-4-DEMETHOXYDAUNOMYCINONE

The present invention relates to the stereospecific synthesis of R(−)-4-demethoxy-7-deoxy-daunomycinone, an intermediate in the synthesis of (+)-4-demethoxydaunomycinone, the aglycone of the non-naturally occurring and antitumor active (−)7(S)9(S)-4-demethoxydaunorubicin. The present invention also pertains to certain novel intermediates.

BACKGROUND OF THE INVENTION

4-Demethoxydaunorubicin is an anthracycline derivative known to have antitumor activity as reported by F. Arcamone et al. in Cancer Treatment Reports, Vol. 60(7), pages 829–834 (1976). Several syntheses of 4-demethoxydaunomycinone from 4-demethoxy-7,9-dideoxydaunomycinone have been described in the literature. See, for example, Suzuki et al., Tetrahedron Letters, p. 2303 (1977) and Kerdesky et al., J. American Chem. Soc., 100(11), p. 3635 (1978).

In the past, little effort was expended in the preparation of optically active aglycones. Such optically active compounds would avoid the very complex separation of diastereomeric products in the final glycosidation step and, of course, would save the valuable sugar moiety.

Past procedures used to obtain optically active aglycones make use of an optically active tetralin as an A B synthon, that has been prepared by resolution of racemic material, as shown in Arcamone et al. German Pat. No. 2,601,785 or Broadhurst et al. J.C.S. Chem. Commun. p. 158 (1982), or by asymmetric systhesis, as shown by Terashima et al. Tetrahedron Letters, p. 2753 (1980) or Warrener et al. J.C.S. Chem. Commun. p. 1100 (1981). The chiral bicyclic compound is then transformed into a tetracyclic intermediate using the synthetic sequence shown in Wong et al., Canadian J. Chem. 49, p. 2712 (1971). This approach suffers from a lack of regiochemical control in the preparation of ring D substituted anthracyclinones, and results in very difficult to achieve regioisomer separation as shown by Wong et al. Canadian J. Chem. 51, p. 466 (1973).

SUMMARY OF THE INVENTION

In accordance with the present invention, the known compound 4-demethoxy-7,9-dideoxydaunomycinone, which compound may be derived from an o-quinodimethane and methyl vinyl ketone by the method generally described in Kerdesky et al. J. American Chem. Soc., 100(11) p. 3635 (1978) is used as the starting material to produce R(−)-4-demethoxy-7-deoxy-daunomycinone. This letter compound is an intermediate in the synthesis of (+)-4-demethoxydaunomycinone, the aglycone of the non-naturally occurring and biologically active (−)7(S)9(S)-4-demethoxydaunorubicin (having antitumor activity). The process of the present invention involves:

(a) reacting 8-acetyl-6,11 dihydroxy-7,8,9,10-tetrahydro-5,12-naphthacenedione, commonly called 4-demethoxy-7,9-dideoxy-daunomycinone(1) with bromine in a lower carboxylic acid, such as acetic acid, in the presence of hydrogen bromide at a temperature in the range of 80°–120° C. to form its 8-bromo derivative(2).

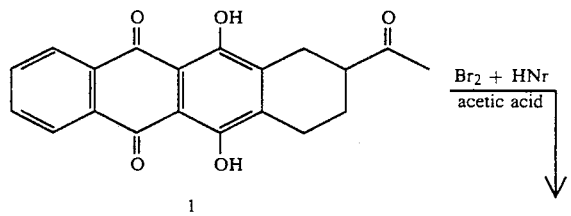

(b) dehydrohalogenation of the 9-bromo derivative(2) with an alkali carbonate, preferably lithium carbonate in a dimethyl acid amide, such as dimethyl formamide to give the enone(3).

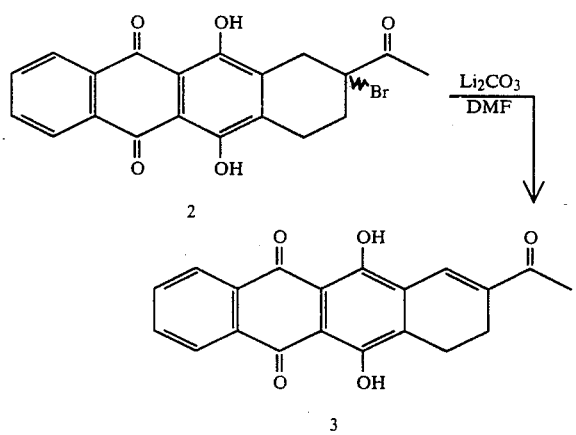

(c) conversion of the enone(3) to the diester derivative(4) by treatment with a lower carboxylic acid anhydride, such as acetic anhydride.

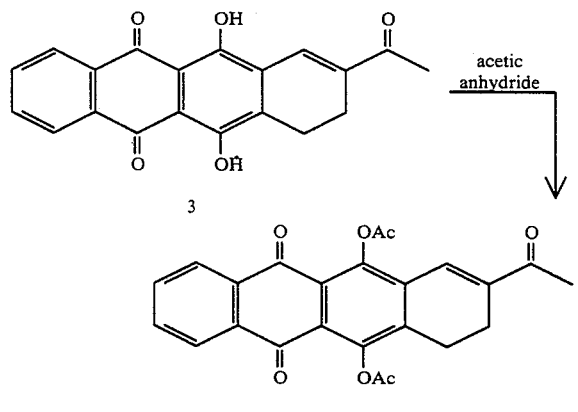

(d) sodium borohydride reduction of the diester derivative(4) preferably in the presence of ceric chloride to give the racemic allylic alcohol(5).

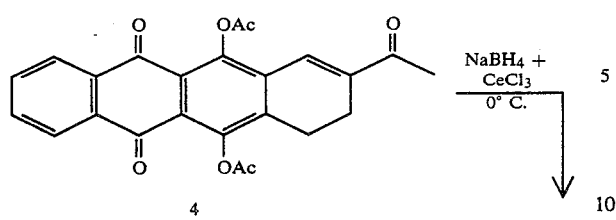

4

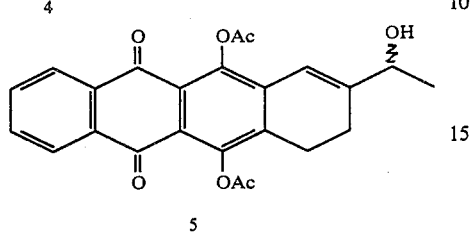

5

(e) asymmetric epoxidation of the racemic allylic alcohol(5) with titanium isopropoxide, (+)-diisopropyl L-tartrate and 0.6 equivalents of an alkyl hydroperoxide, most preferably tert-butyl hydroperoxide to give a mixture of the erythro epoxide (—)(6) and the R(+) allylic alcohol(5a).

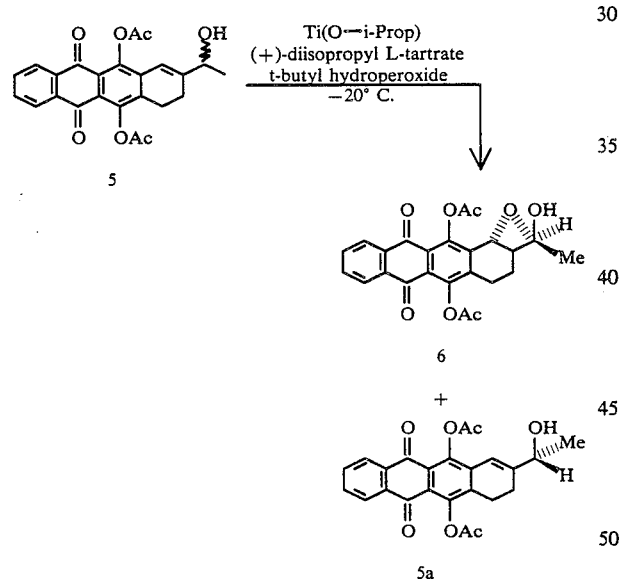

(f) the mixture of (5a) and (6) is treated with an excess of chromic acid to give a mixture of (—)-epoxy ketone(7) and the diester derivative(4).

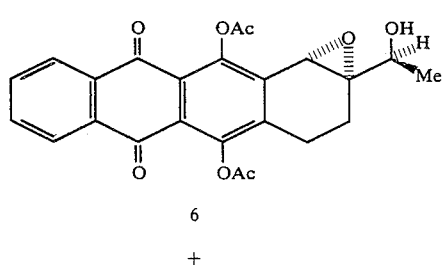

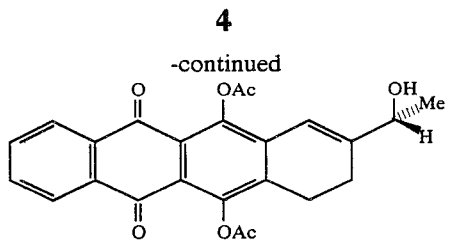

5a chromic acid
aqueous solution

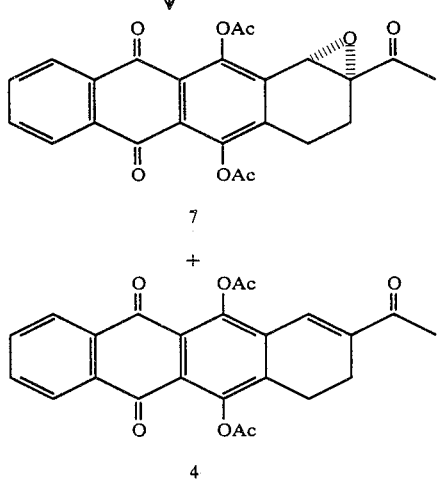

7

+

4

(g) separate (4) and (7) by crystallization and reduce the (—)-epoxy ketone(7) with an excess of sodium dithionite most preferably in the presence of sodium hydroxide to give R(—)-4-demethoxy-7-deoxydaunomycinone(8). The separated diester derivative(4) can be returned and used in step (d) of the synthesis.

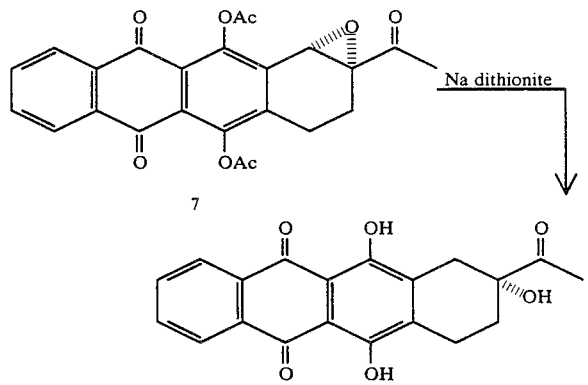

8

Parenthetically, in the above formulas as well as in other structural formulas appearing herein, some of the hydrogen atoms are omitted for the sake of clarity. Those skilled in the art will have no trouble comprehending the formulas to include the omitted hydrogen atoms. It should also be noted that in the above formulas, and elsewhere herein, the use of "Ac" is understood to represent the acetyl radical, i.e.,

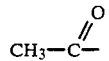

DESCRIPTION OF PREFERRED EMBODIMENTS

The preferred embodiments of this invention are further illustrated by the following examples in which the parts and percentages are by weight.

EXAMPLE

To a solution of 7 grams of 8-acetyl-6,11 dihydroxy-7,8,9,10-tetrahydro-5,12-naphthacenedione(1) in a mixture of 150 milliliters of acetic acid containing 1 milliliter of 40% aqueous hydrogen bromide, is added 29.4 milliliters of a 0.71M solution of bromine in acetic acid. The resulting solution is stirred at room temperature for 5 hours and then heated at a temperature of 100°–110° C. for 20 hours. On cooling the 8-acetyl-8-bromo-6,11-dihydroxy-7,8,9,10-tetrahydro-5,12-naphthacenedione(2) crystallizes as orange crystals having a melting point of 219°–221° C. Analysis of the product by nuclear magnetic resonance gives the following—$\delta 2.07$ (m, 1H, H-9), 2.53 (m, 1H, H-9), 2.57 (s, 3H, COCH$_3$), 3.12 (m, 2H, H-10), 3.44 and 3.61 (ABq, J$_{AB}$: 19Hz, 2H, H-7), 7.83 (m, 2H, Ar), 8.34 (m, 2H, Ar), 13.44 (s, 1H, OH), 13.49 (s, 1H, OH). Infrared analysis shows peaks at 1708 (CO), 1624 (H-bonded quinone), and 1587 cm$^{-1}$ (Ar). Ultra violet-visible analysis of the product in CH$_3$CN $\lambda$ max. shows peaks at 249 (log $\epsilon$ 4.55), 287 (3.96), 320 (3.36), 449 (4.01), 471 (4.04), and 500 nm (3.85). Analysis by mass spectrometer gives the following—m/e 414 (M+, 4), 335 (100), 334 (56), 332 (37), 317 (24), 301 (18), 293 (23), 292 (22), and 291 (46). Analysis for molecular weight calculated for C$_{20}$H$_{15}$O$_5$Br is 414.0102, found by high resolution mass spectrum is 414.0043.

To a suspension of 6.90 grams of the 8-acetyl-8-bromo-6,11-dihydroxy-7,8,9,10-tetrahydro-5,12-naphthacenedione in 150 milliliters of dimethyl formamide, 7 grams of lithium carbonate is added. The resulting mixture is stirred at room temperature, under nitrogen atmosphere, for 24 hours and then warmed to 60°–70° C. for 6 hours. The purple solution is allowed to cool and slowly poured into 500 milliliters of an ice-water mixture containing 100 milliliters of 12% hydrochloric acid. A reddish brown precipitate is separated by filtration, washed with water and dried. Crystallization from absolute ethyl alcohol-chloroform yields 8-acetyl-6,11-dihydroxy-9,10-dihydro-5,12-naphthacenedione(3) having a melting point of 235°–237° C. Analysis of the product by nuclear magnetic resonance gives the following—2.53 (s, 3H, COCH$_3$), 2.66 (t, J: 9Hz, 2H, H-9), 3.00 (t, J: 9Hz, 2H, H-10), 7.84 (m, 2H Ar), 7.87 (s, 1H, H-7), 8.36 (m, 2H, Ar), 13.25 (s, 1H, OH), 13.58 (s, 1H, OH). Infrared analysis shows peaks at 1660 (CO), 1621 (H-bonded quinone), and 1584 cm$^{-1}$ (Ar). Ultra violet-visible analysis of the product in CH$_3$CN $\lambda$ max. shows peaks at 282 (log $\epsilon$ 4.57), 298 (4.53), and 493 nm (4.05). Analysis by mass spectrometer gives the following—m/e 334 (M+, 100), 332 (43), 319 (24), 317 (25), 316 (18), 301 (50), and 291 (82). Elemental analysis calculated for C$_{20}$H$_{14}$O$_5$:C, 71.85; H, 4.22; found C, 71.64; H, 4.31.

A suspension of 5.4 grams of 8-acetyl-6,11-dihydroxy-9,10-dihydro-5,12-naphthacenedione(3) in a mixture of 100 milliliters of pyridine and 35 milliliters of acetic anhydride is stirred at room temperature for 4 hours. The solvent is removed in vacuo, the gummy residue taken up in chloroform and washed with water, dilute aqueous hydrochloric acid and then water. Crystallization from absolute ethyl alcohol-chloroform yields light yellow crystals of 8-acetyl-6,11-diacetoxy-9,10-dihydro-5,12-naphthacenedione(4) having a melting point of 232°–234° C. Analysis of the product by nuclear magnetic resonance gives the following—$\delta 2.43$, 2.53 and 2.58 (s, 3 each, 2xOAC and COCH$_3$), 2.6–2.9 (m, 4H, H-9 and H-10), 7.50 (s, 1H, H-7), 7.74 (m, 2H, Ar) and 8.13 (m, 2H, Ar). Infrared analysis shows peaks at 1760 (broad, ArOAc), 1665 (COCH$_3$), 1595 and 1575 cm$^{-1}$ (Ar). Ultra violet-visible analysis of the product in CH$_3$CN $\lambda$ max. shows peaks at 253 (log $\epsilon$ 4.36), 285 (4.66), 293 (4.60), and 365 nm (3.95). Analysis by mass spectrometer gives the following—m/e 418 (M+, 1), 376 (13), 334 (100), 332 (12), 301 (16), and 291 (28). Elemental analysis calculated for C$_{24}$H$_{18}$O$_7$: C, 68.90; H, 4.34; found C, 68.75; H, 4.51.

To a solution of 1 gram of the 8-acetyl-6,11-diacetoxy-9,10-dihydro-5,12-naphthacenedione(4) and 0.89 gram of ceric chloride (CeCl$_3$·7H$_2$O) in a mixture of 10 milliliters of methyl alcohol and 30 milliliters of chloroform at a temperature of 0° C. is added portion wise with stirring 0.091 gram sodium borohydride. The solution is held at a temperature of 0° C. for 20 minutes, then poured into water and heated in a steam bath for 5 minutes under an air stream. After cooling, the organic phase is separated and washed with water. Removal of the solvent and trituration of the residue with hexane-ether yields an amorphous yellow powder of 8-(1-hydroxyethyl)-6,11-diacetoxy-9,10-dihydro-5,12-naphthacenedione(5) having a melting point of 183°–185° C. Analysis of the product by nuclear magnetic resonance gives the following—$\delta$ 1.37 (d, J: 6.5Hz, 3H, CH$_3$), 2.52 (s, 3H, OAc), 2.53 (s, 3H, OAc), 2.3–2.9 (m, 4H, H-9 and H-10), 4.48 (m, 1H, CHOH), 6.67 (s, 1H, H-7), 7.72 (m, 2H, Ar), and 8.14 (m, 2H, Ar). Infrared analysis shows peaks at 3500 (OH), 1777 (ArOAc), 1679 and 1665 (quinone and C=O), and 1575 cm$^{-1}$ (Ar). Ultra violet-visible analysis of the product in CH$_3$CN $\lambda$ max. shows peaks at 252 (log $\epsilon$ 4.10), 285 (4.36), and 377 nm (3.57). Analysis by mass spectrometer gives the following—m/e 420 (M+, 2), 378 (23), 360 (11), 336 (100), 334 (30), 320 (67), and 318 (92). Elemental analysis calculated for C$_{24}$H$_{20}$O$_7$: C, 68.57; H, 4.80; found C, 68.28; H, 5.03.

To a cooled solution of 338 milligrams of titanium isopropoxide in 5 milliliters of dichloromethane is added 338 milligrams of diisopropyl L-tartrate. The resulting mixture is stirred under nitrogen, at −20° C., for five minutes. Then, a solution of 0.5 gram of 8-(1-hydroxyethyl)-6,11-diacetoxy-9,10-dihydro-5,12-naphthacenedione(5) and 72 milligrams of 90% tert.-butyl hydroperoxide in 2 milliliters of dichloromethane is added. The reaction mixture is stirred at −20° C. for 2 hours and then kept in a freezer at −20° C. for 15 hours. The cooled reaction mixture is poured into water and the organic phase separated, dried and concentrated. Trituration of the residue with ether yields a yellow powder, which is shown by nuclear magnetic resonance analysis to be a mixture of (+)-8-[(1R)-1-hydroxyethyl]-6,11-diacetoxy-9,10-dihydro-5,12-naphthacenedione (5a) and (−)-(7S, 8S)-8-[(1S)-1-hydroxyethyl]-7,8-epoxy-6,11-diacetoxy-9,10-dihydro-5,12-naphthacenedione (6).

To 20 milliliters of dichloromethane is added 399 milligrams of the above mixed product (6 and 5a). The resulting solution is treated with an excess of aqueous chromic acid (18 milliliters of 0.08M aqueous solution) and stirred at room temperature for 6 hours. The organic phase is separated, washed with water and filtered through a silica gel column using dichloromethane and ethyl acetate to give a crude mixture of (—)-8-acetyl-7,8-epoxy-6,11-diacetoxy-9,10-dihydro-5,12-naphthacenedione(7) and 8-acetyl-6,11-diacetoxy-9,10-dihydro-5,12-naphthacenedione(4)/ Crystallization of the mixed product from ethylacetate gives light yellow crystals of (—)-8-acetyl-7,8-epoxy-6,11-diacetoxy-9,10-dihydro-5,12-naphthacenedione(7) having a melting point of 235°–237° C. and $[\alpha]_D$; —98° (c 0.57 in CHCl$_3$). Analysis of the product by nuclear magnetic resonance gives the following—$\delta$2.25 (s, 3H, CH$_3$), 2.52 (s, 3H, OAc), 2.59 (s, 3H, OAc), 2.3–3.1 (m, 4H, H-9 and H-10), 4.33 (s, 1H, H-7), 7.75 (m, 2H, Ar) and 8.16 (m, 2H, Ar). Infrared analysis shows peaks at 1770 (ArOAc), 1704 (CO), 1678 (quinone), and 1587 cm$^{-1}$ (Ar). Analysis by mass spectrometer gives the following—m/e 434 (M+, 0.2), 392 (6), 350 (52), 332 (20), 322 (12) and 308 (100). Elemental analysis calculated for C$_{24}$H$_{18}$O$_8$: C, 66.36; H, 4.18; found C, 66.18; H, 4.01.

To a solution of 240 milligrams of sodium hydroxide and 510 milligrams of sodium dithionite in 60 milligrams of water is added 60 milligrams of (—)-8-acetyl-7,8-epoxy-6,11-diacetoxy-9,10-dihydro-5,12-naphthacenedione(7) with stirring under nitrogen. The resulting mixture is stirred for 1 hour at room temperature, then air is bubbled through for 10 minutes. The air bubbling is continued for another 10 minutes while the reaction mixture is acidified with dilute hydrochloric acid. The resulting red precipitate is separated by filtration and purified by silica gel chromatography using dichloromethane and ethyl acetate to yield R(—)-4-demethoxy-7-deoxydaunomycinone(8) having a melting point of 201°–203° C. and $[\alpha]_D$; —71° (c 0.15 in CHCl$_3$). Analysis by thin layer chromatography, nuclear magnetic resonance, and infrared spectra shows that the product is identical with an authentic sample of R(—)-4-demethoxy-7-deoxydaunomycinone(8).

What we claim and desire to protect by Letters Patent is:

1. A process for making R(—)-4-demethoxy-7-deoxydaunomycinone comprising (a) selectively brominating 8-acetyl-6,11-dihydroxy-7,8,9,10-tetrahydro-5,12-naphthacenedione to form its 8-bromo derivative having the formula

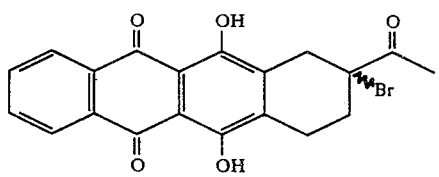

(b) dehydrohalogenating the 8-bromo derivative with an alkali carbonate to form the enone derivative having the formula

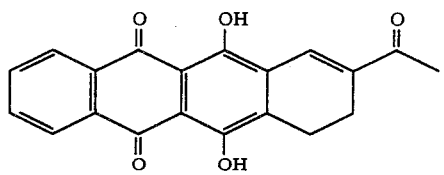

(c) esterifying the enone derivatives with a lower carboxylic acid anhydride to form the diester derivative having the formula

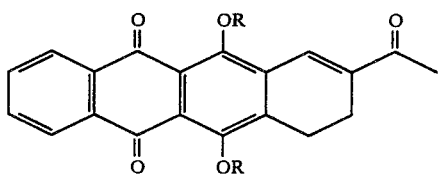

where R is a lower alkyl acyl radical.

(d) reducing the diester derivative with sodium borohydride to give the racemic allylic alcohol having the formula

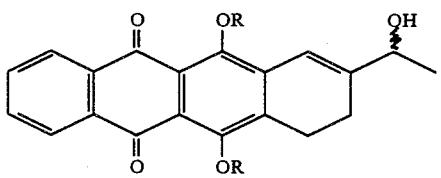

(e) asymmetrically epoxidizing the racemic allylic alcohol with titanium isopropoxide, (+)-diisopropyl L-tartrate and an alkyl hydroperoxide to give a mixture of the erythro epoxide (—) and the R (+) allylic alcohol having the formulas

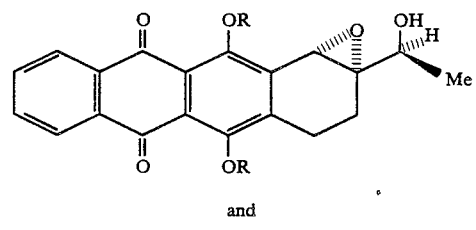

and

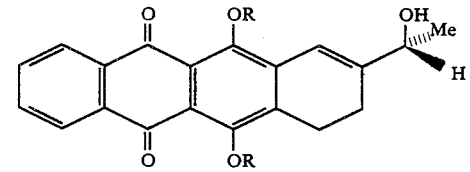

(f) oxidizing the above mixture with chromic acid to give a mixture of the (—)-epoxy ketone and the diester derivative having the formulas

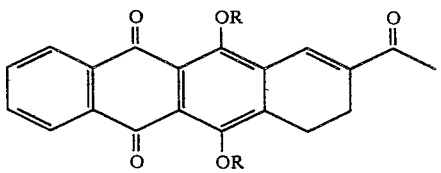

-continued and

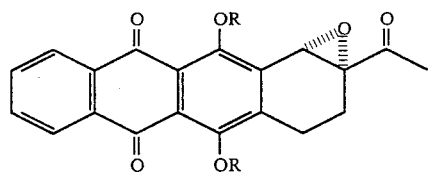

(g) separating the (—)-epoxy ketone from the diester derivative by crystallization and reducing (—)-epoxy ketone with sodium dithionite to give R(—)-4-demethoxy-7-deoxydaunomycinone having the formula

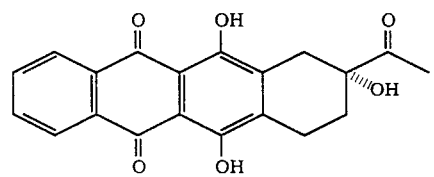

2. 8-Acetyl-8-bromo-6,11-dihydroxy-7,8,9,10-tetrahydro-5,12-naphthacenedione having the formula

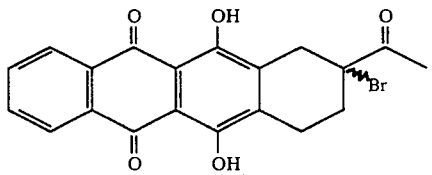

3. 8-(1-Hydroxyethyl)-6,11-diacetoxy-9,10-dihydro-5,12-naphthacenedione having the formula

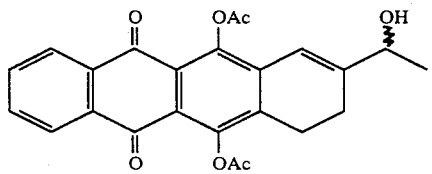

4. (+)-8-[(1R)-1-Hydroxyethyl]-6,11-diacetoxy-9,10-dihydro-5,12-naphthacenedione having the formula

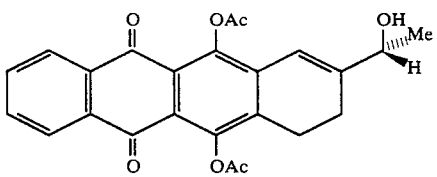

5. (—)-(7S, 8S)-8-[(1S)-1-hydroxyethyl)]-7,8-epoxy-6,11-diacetoxy-9,10-dihydro-5,12-naphthacenedione having the formula

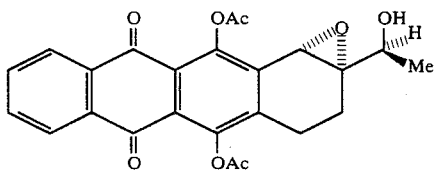

* * * * *

UNITED STATES PATENT AND TRADEMARK OFFICE
CERTIFICATE OF CORRECTION

PATENT NO. : 4,489,206
DATED : December 18, 1984
INVENTOR(S) : Michael P. Cava and Domingo Dominguez (Case 2)

It is certified that error appears in the above-identified patent and that said Letters Patent are hereby corrected as shown below:

Col. 2, formula 1, " $Br_2 + HNr \xrightarrow{\text{acetic acid}}$ " should read -- $Br_2 + HBr \xrightarrow{\text{acetic acid}}$ --.

[SEAL]

Signed and Sealed this

Twenty-first Day of May 1985

Attest:

DONALD J. QUIGG

Attesting Officer

Acting Commissioner of Patents and Trademarks